United States Patent
Booker et al.

(10) Patent No.: US 6,974,416 B2
(45) Date of Patent: Dec. 13, 2005

(54) DOPPLER PROBE WITH SHAPEABLE PORTION

(75) Inventors: Robert Booker, Vandergrift, PA (US); Chun Kee Lui, Monroeville, PA (US); Bill Boyle, Lower Burrell, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 275 days.

(21) Appl. No.: 09/925,693

(22) Filed: Aug. 9, 2001

(65) Prior Publication Data

US 2002/0049385 A1 Apr. 25, 2002

Related U.S. Application Data (60) Provisional application No. 60/225,862, filed on Aug. 16, 2000.

(51) Int. Cl.$^7$ ................................................ A61B 8/00
(52) U.S. Cl. ....................................... 600/459; 600/461
(58) Field of Search ................................ 600/437, 443, 600/442, 461, 462, 459, 460, 463, 464, 444, 447, 455, 454

(56) References Cited

U.S. PATENT DOCUMENTS

| | | | | |
|---|---|---|---|---|
| 128,639 A | * | 7/1872 | Pless et al. ................... | 278/57 |
| 5,398,689 A | | 3/1995 | Connor et al. | |
| 5,464,016 A | * | 11/1995 | Nicholas et al. ............ | 600/463 |
| 5,503,155 A | * | 4/1996 | Salmon et al. ............... | 600/463 |
| 5,655,537 A | * | 8/1997 | Crowley ....................... | 600/446 |
| 5,775,328 A | | 7/1998 | Lowe et al. | |
| 5,931,788 A | | 8/1999 | Keen et al. | |
| 5,938,615 A | | 8/1999 | Eberle et al. | |
| 6,036,645 A | | 3/2000 | Drost et al. | |
| 6,164,277 A | * | 12/2000 | Merideth ...................... | 128/207.14 |
| 6,216,233 B1 | * | 4/2001 | Baweja ......................... | 365/222 |
| 6,340,356 B1 | * | 1/2002 | Navia et al. ................. | 604/104 |

FOREIGN PATENT DOCUMENTS

| | | |
|---|---|---|
| EP | 0453071 | 10/1991 |
| WO | 9744089 | 11/1997 |

* cited by examiner

Primary Examiner—Marvin M. Lateef
Assistant Examiner—Maulin Patel
(74) Attorney, Agent, or Firm—Brinks Hofer Gilson Lione (57) ABSTRACT

Disclosed is ultrasonic medical probe (10) connectable to a Doppler signal generator and processor for detecting or measuring blood flow in a vessel. In one embodiment, the distal portion (52) of the probe comprises an outer sheath (17) that includes a malleable shapeable portion (16), such as an annealed stainless steel cannula, to which a transducer head (11) containing one or more ultrasonic transducers (12), is mounted distally. Two wires (14, 15), comprising the electrical conductor (13), extend through the outer sheath from each ultrasonic transducer to a proximal connector (19). The shapeable portion can be contoured before or during a procedure, such as to access the natural spaces within brain to read flow in a cerebral artery. Other disclosed embodiments includes a shapeable portion that includes a malleable core wire (33) around which the wires are wrapped, an electrical conductor comprising malleable wires (36, 37) that are shapeable, a transducer head that is extendable from inside the outer sheath, and a handle portion (18) that is axially moveable for adjusting the length of the shapeable portion.

46 Claims, 3 Drawing Sheets

DOPPLER PROBE WITH SHAPEABLE PORTION

RELATED APPLICATION

This application claims priority of provisional application Ser. No. 60/225,862, filed Aug. 16, 2000.

TECHNICAL FIELD

This invention relates to medical devices, more particularly to medical probes utilizing Doppler signals to measure flow of bodily fluids.

BACKGROUND OF THE INVENTION

A cerebral aneurysm represents a serious medical condition in which a lesion on a vessel within the crevices of the brain weakens, allowing the vessel wall to expand outward like a balloon. It is estimated that perhaps 2% of the general population live with a cerebral aneurysm, most of which go undetected until the aneurysm suddenly ruptures and causes a subarachnoid hemorrhage in the brain. While the mortality rate from hemorrhage is high (up to 50% within the first two weeks, with many of these occurring immediately), many of the survivors can be spared serious neurological injury or subsequent hemorrhage if treated in a timely manner.

One method of treating cerebral aneurysms involves the use of a plastic or metallic surgical clip that is delivered to the site of the aneurysm to clamp and temporarily or permanently close the vessel or a portion thereof to either prevent further bleeding or prevent rupture, if the aneurysm has been diagnosed in time. One recurrent problem with clipping of the vessels, especially in hard-to-access regions such as within the brain, is that it is difficult to ascertain the presence or absence of blood flow within the vessels before and after the clip has been applied. Of particular concern is the accidental clipping off of non-target branch or vessel. For example, if attempt to treat an aneurysm by clipping either the internal or external carotid arteries which branch from the common carotid supplying blood to the brain, it would be catastrophic, if during application of the clip to cut off flow to one branch, the clip also accidentally cuts off flow to the opposite branch as well.

Ultrasonic Doppler probes have proven to be efficacious in detecting blood flow in a vessel. One such use of Doppler involves monitoring blood flow following vessel anastomosis as a part of organ transplant, reconstructive surgery, and other procedures where small vessels must be reattached and can frequently close off following surgery. Instruments developed for this purpose have involved securing the Doppler transducer head to the vessel, such as with a cuff, then closing the incision with the conductor wires exiting the patient where they are attached to an appropriate ultrasound frequency generator, back-scattering sensor, and control computer. While this has proven to be an effective means of providing longer term monitoring of vessel patency, such a device would not be appropriate when only a single reading is required at multiple locations, such as when clipping an aneurysm, a procedure normally performed using a neuroendoscope. Within the brain, reaching and properly positioning a probe can be problematic due to the restricted space in which to work. Naturally, rigid probes are very limited in their ability to be properly positioned, and flexible probes cannot be controlled sufficiently to be able to assuredly place the transducer at a particular site. Even deflectable catheters are limited in their ability to be adequately maneuvered due to the difficult anatomical constraints typically encountered in attempting to reach a target cerebral vessel, something which can require a series of different bends to achieve the ultimate desired angle of the transducer head.

Therefore, what is needed is an ultrasonic Doppler probe that can be introduced intracranially and manipulated to the desired configuration for traversing the natural spaces, i.e., the ventricles and cisterns, of the brain to measure blood flow at a particular site upon a cerebral vessel to help determine whether an aneurysm has been successfully treated. Furthermore, such as device should be able to be used in combination with standard neuroendoscopes.

SUMMARY OF THE INVENTION

The foregoing problems are solved and a technical advance is achieved in an illustrative ultrasonic Doppler probe comprising a transducer head with an ultrasonic Doppler transducer connected to a conductor means, and further including a shapeable distal portion for manually configuring the probe to access a particular anatomical site to confirm blood flow in a vessel. In the illustrative embodiment which is used to establish whether an aneurysm clip has been properly applied to an affected cerebral vessel, the shapeable portion comprises a malleable outer sheath comprising a thin-walled stainless steel cannula that has been annealed. This allows it to be sufficiently ductile such that, prior to insertion into the patient, after ascertaining the particular shape of the intracranial spaces, the operator can manipulate the shapeable portion to the necessary shape to achieve a desired pathway to the target site. The transducer crystal is soldered to the conductor means, consisting of two wires, which have been angled to orient the crystal such that is perpendicular with the longitudinal axis of the probe and can only read in one direction. In a different embodiment, the Doppler ultrasonic crystal is oriented parallel with the longitudinal axis of the probe, therefore being able to simultaneously detect flow from either direction, relative the transducer head. Further embodiments could include orienting the Doppler ultrasonic crystal at any angle between perpendicular and parallel to the longitudinal axis of the probe.

To protect the crystal, it is encased in a protective material, such as epoxy, to form the transducer head which is applied directly to the vessel surface to detect possible blood flow. The conductive wires extend through the shapeable cannula portion where they are encased in a polymer sleeve and form a proximal connector, which is connectable to a Doppler signal generating unit, such as the COOK® Vascular Blood Flow Monitor, which generates a 20 MHz Doppler signal that can, with the probe, allow it to sense pulsative blood flow within the vessel within a distance of about 8–10 mm. This movement is detected by the transducer crystal and the signal is processed and converted by the unit to an audible signal. If the transducer head is placed upon an area that lacks pulsative flow, such as an occluded vessel, there is no audible signal generated by the external unit. The transducer head may also include at least a second Doppler ultrasonic crystal such that the probe can be adapted to measure actual flow rates within the vessel, instead of relative flow velocity.

In another aspect of the invention, the shapeable portion of the probe comprises a separate component, e.g., an outer sheath, through which an inner member is introduced. In this embodiment, the transducer head is attached distally to the inner member and can remain housed within the outer malleable sheath until deployment at the site where the reading is to be taken.

In yet another aspect of the invention, the shapeable portion comprises a solid wire to which the transducer head is attached. The conductor wires extend externally along the shapeable wire with an outer polymer sleeve providing protection and support to the conductor wires.

In still yet another aspect of the invention, the conductor means itself comprises the shapeable portion. In one embodiment, the smaller diameter conductor wires that are connected to the crystal are, in turn, connected to larger diameter conductor wires that can be malleably shaped to a desired configuration, thus obviating the need for a separate malleable component such as a sheath or core wire.

In still yet another embodiment of the present invention, the length of the shapeable portion is made adjustable by allowing the handle to be repositioned relative to the outer sheath. The handle includes a tightening mechanism, such as a set screw or collet, that allows it to be secured to the sheath which extends through the lumen of the handle.

BRIEF DESCRIPTION OF THE DRAWINGS

Embodiments of the present invention will now be described by way of example with reference to the accompanying drawings, in which.

DETAILED DESCRIPTION

FIGS. 1–9 depict various embodiments of the present invention, which comprises a malleable medical probe 10 that utilizes ultrasonic Doppler signals to detect and confirm the presence of flow within a vessel, such as a cerebral artery or vein. The illustrative probe 10 primarily comprises a transducer head 11 located about the distal end 26 of an outer sheath 17 that houses at least a portion of an electrical conductor 13 extending from the transducer head 11 to which the first end 63 of the electrical conductor 13 is connected. A handle portion 18 is included in the illustrative embodiments which is connected about the outer sheath 17. That portion of the outer sheath 17 and/or electrical conductor 13 that extends distally from the handle portion 18 is generally defined as the shapeable portion 16 of the probe 10, although the portion of the shapeable portion 16 closest to the handle portion 18 may not be intended to be malleable or shapeable. Additionally, the portion of the outer sheath 17 or electrical conductor 13 located within or proximal to the handle portion 18 may be as inherently malleable or shapeable as the shapeable portion 18 itself.

Figure 1:
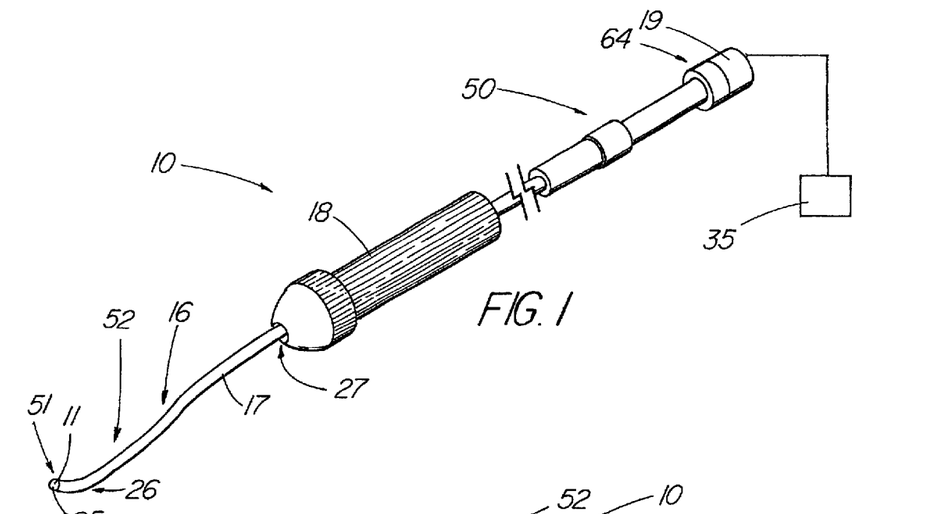
FIG. 1 depicts a pictorial view of the illustrative embodiment of the present invention.
Figure 2:
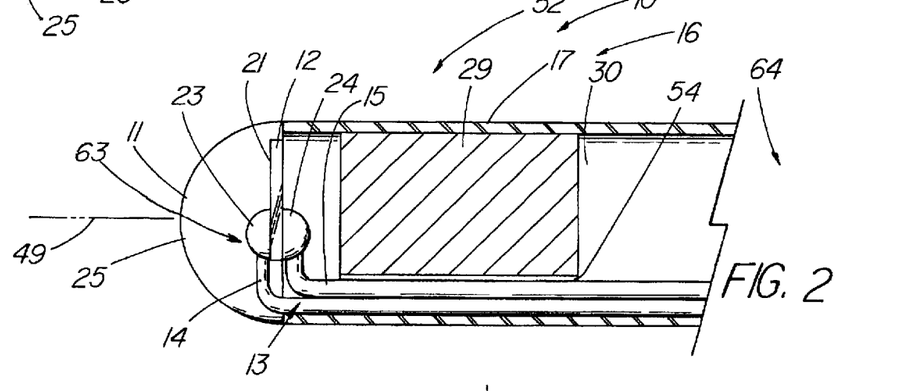
FIG. 2 depicts a partially sectioned side view of the embodiment of FIG. 1.

As shown in the illustrative embodiment of FIGS. 1–2, the probe 10 includes a transducer head 11 at its distal end 51, the transducer head comprising an ultrasonic transducer 12, such as a 1 mm diameter, 20 MHz Valpey-Fisher High Density Lead Zirconate Titanate Compressional Crystal (Model No. HD 3195) with a fine ground finish and chrome/gold electrodes on both sides. The ultrasonic transducer 12 is mounted with the first operative surface 21 facing directly forward such that the ultrasonic transducer 12 is oriented perpendicular to the longitudinal axis 49 of the probe 10. Extending proximally from the ultrasonic transducer 12 is electrical conductor 13, which in the illustrative embodiment includes a first and a second wire 14, 15 such as 36 AWG stranded, silver plated wires coated with polytetrafluoroethylene (PTFE). The two wires 14, 15 must be bent at approximately a 90° angle from the longitudinal axis 49 so that they can be attached to the respective oppositely placed electrodes on the ultrasonic transducer 12 by means such as soldering (depicted as first and second solders joints 23 and 24). The wires 14, 15 extend proximally where they may connect to other wires. The illustrative second end 64 of the illustrative electrical conductor 13 eventually terminates at a proximal connector 19 which includes pins for connecting to a unit 35 that generates and processes the Doppler signal, such as the COOK® Vascular Blood Flow Monitor (Cook Vascular, Incorporated, Leechburg, Pa.).

To form the transducer head 11 of the illustrative embodiment, the assembly comprising the ultrasonic transducer 12 and soldered wires 14, 15 is placed into position about the distal end 26 of the outer sheath 17 which houses at least the distal portion of the electrical conductor 13 (wires 14 and 15). The epoxy comprising the encasing material 25 is mixed and the probe 10 is hung upside down. Epoxy is then continually added to the ultrasonic transducer 12 and distal end 26 of the outer sheath 17 until it is no longer being drawn up inside, whereby a dome is created that completely encases the ultrasonic transducer 12. It is most desirable that the distal portion 52 comprising the transducer head 11 and shapeable portion 16 being isodiametric for a smooth transition between the different components. Insuring that no air bubbles have formed, the probe 10 is allowed to cure for 4 to 6 hours. Some optional curing in an oven may be possible to finish the process after the epoxy has cured for the minimum 4–6 hour time period. Otherwise, the transducer head will not fully cure until the probe 10 has been allowed to sit overnight. Alternatively, a UV curable encasing material 25 may be used for a more rapid cure. Other sufficiently durable materials capable of transmitting Doppler signals may be suitable, as well (e.g, glass, polyacrylates, etc.).

To assist in the manipulation and operation of the probe 10, the handle 18 is conveniently located along a portion of the device that remains external to the patient. The handle 18 also advantageously provides protection to the junction where the wires 14, 15 extending from the transducer head 11 are connected to the proximal portion 50 of the device, which in the illustrative embodiment is a flexible assembly of shrink tubing, other silicone tubing, and the proximal connector 19. These components of the proximal portion 50 serve to protect the wires 14, 15 as they extend proximally from the handle 18 and provide a flexible extension means to connect the remainder of the probe 10 to the external source unit 35.

Figure 3:
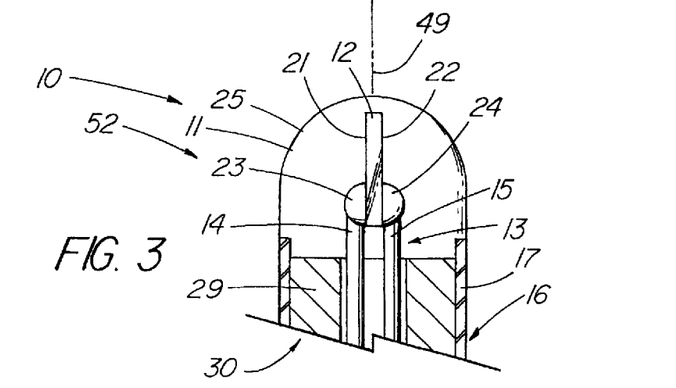
FIG. 3 depicts a partially sectioned side view of an embodiment wherein the ultrasonic transducer crystal is oriented parallel to the longitudinal axis of the probe.

FIG. 3 depicts an embodiment in which the crystal comprising the ultrasonic transducer 12 is oriented parallel with the longitudinal axis 49 of the probe 10, rather than being perpendicular thereto. It should be noted that for purposes of interpreting the claims and specification, the longitudinal axis 49 is defined as that which extends lengthwise through and along the malleable sheath in its straight configuration, prior to any plastic reshaping that occurs. The parallel orientation of FIG. 3 allows the ultrasonic transducer 12 to have both a first operative 21 surface facing laterally one direction and a second operative surface 22 facing in an opposite direction to simultaneously detect movement from flow from either direction. This feature can be advantage or a disadvantage according to the particular clinical use of the device as it is generally impossible to determine the true source of the signals indicating flow. If desired, more than one ultrasonic transducer 12 can be mounted within the transducer head 11, facing oppositely and each with a single, first operative surface 21, to permit bidirectional sensing with separate processing of the Doppler signals, this permitting the operator to specifically determine from which direction the signals are being sensed according to which ultrasonic transducer is making the reading.

Again referring to FIGS. 1 and 2, an important point of novelty in the illustrative invention lies in the addition of a shapeable portion 16 to the probe that allows the physician to generally customize the configuration of the distal portion 52 of the device that is introduced into the patient to precisely place the transducer head 11 at the target site. The shapeable portion 16 comprises at least much of the distal portion 52 of the probe 10 and is characterized as the region of the probe that due to its materials and method of construction, allows it to be plastically deformed immediately prior to, or during the procedure such that it generally holds its new shape as it is being manipulated within the patient. If necessary, the shapeable portion 16 must be able to be further plastically manipulated to assume additional new shapes as needed during the course of a normal medical procedure. It should be noted that the probe 10 may be pre-configured prior to packaging such that the shapeable portion 16 includes predetermined shape, such as 90° bend. Such a bend or shape may be set into the shapeable portion 16 such that the areas of the bend are more resistant to further plastic deformation than the regions between the preformed bends.

There are many ways of making a portion of the probe 10 shapeable. In the illustrative embodiment of FIGS. 1–2, this is done by including an outer sheath 17 that is made of a malleable material. The distal end 26 of the malleable outer sheath 17 is affixed to the transducer head 11 and the proximal end 27 terminates inside or proximal to the handle 18 of the probe 10. As previously noted, the distal portion of the malleable outer sheath 17 comprises the shapeable portion 16 of the probe 10. The malleable outer sheath 17 contains a passage 30 through which extend the wires 14, 15 that comprise the conductor means 13. In the illustrative embodiment, the malleable outer sheath 17 comprises a piece of metal cannula, such as a 1/16" OD annealed seamless 304 stainless steel tubing with a 0.010" wall thickness. Annealing makes the metal tubing ductile and thus, able to accept a new shape by the minimal application of manual pressure to change its shape. The combination of cannula diameter, degree of annealing, wall thickness, a metal type, all determine the degree of malleability of the shapeable portion, which should not be overly malleable such that normal contact expected during the procedure can cause the probe to lose its configured shape. While annealed stainless steel makes an excellent material for this purpose, any suitable metal, (e.g., copper, tungsten, titanium, etc.), a metal-polymer composite, or other material can be used that is sufficiently malleable to be able to be plastically reconfigured to a desired shape. While superelastic materials fall within the scope of the invention in that they can be plastically reconfigured by cold working or annealing them under high temperatures, the time and difficulty of the procedures for doing so generally make them less desirable to the physician, who would much prefer to be able to quickly make a series of contour adjustments during the procedure, as needed.

To further protect and support the wires 14, 15, a capture sheath 29 is placed in the passage 30 about the distal end 26 of the outer malleable sheath 17/shapeable portion 16. A passage 54 is created through which the wires 14, 15 extend. The capture sleeve 29 further serves as a surface to which the transducer head can be bonded, providing improved support thereto.

Figure 4:
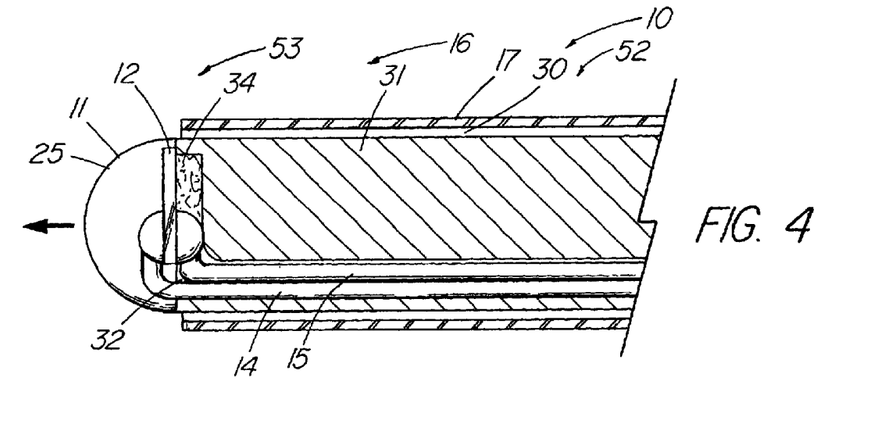
FIG. 4 depicts a partially sectioned side view of an embodiment that includes a malleable outer member and a coaxial inner member.

A second embodiment, in which the shapeable portion 16 comprises an outer metal cannula 17, is depicted in FIG. 4. In this embodiment, the shapeable portion 16 comprises the outer sheath 17, which cooperates with a coaxial inner member 31 that includes the transducer head 11 affixed at its distal end 53. The inner member 31 is made of a flexible material, such as PEBAX®, that has good column strength such that can be retracted or removed during introduction of the probe 10 to protect the transducer head until the probe is near the site of operation. If desired, an obturator (not shown) can be temporarily placed within the distal portion 52 of the probe, possibly via a side port on the handle, to make the distal tip 51 of the probe less traumatic and to prevent tissue or bodily fluids from entering the passage 30 of the outer sheath 17. The probe can also be designed such that the transducer head 11 has both forward and retracted positions, thereby accomplishing these same goals without the use of an obturator. Another variation that is not shown would be to have the outer sheath 17 connected about the distal end 53 of the inner member with a flexible material, such as a fabric or thin polymer sheet, that is bonded to both, thus limiting forward movement of the transducer head 11 relative the outer sheath 17. Depending on the material selected, this would also advantageously seal against fluids entering the passage 30. In the illustrative embodiment, the inner member 31 is affixed to the transducer head 11 which an adhesive or bonding material 34, which could include the same epoxy or other material applied when forming the encasing material 25, or a second or same material that is applied later after the transducer head is formed. The wires extend through a passage 32 created within the inner member where they ultimately terminate in a connector at the proximal end.

Figure 5:
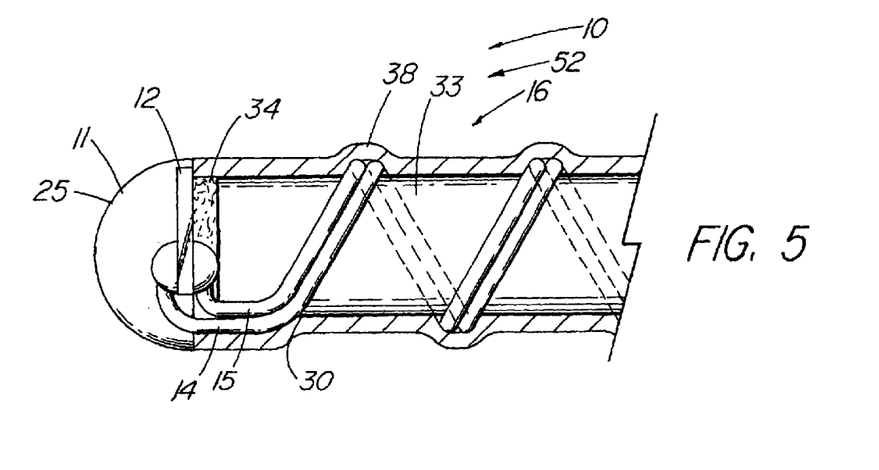
FIG. 5 depicts a partially sectioned side view of an embodiment wherein the malleable portion comprises an inner core wire.
Figure 6:
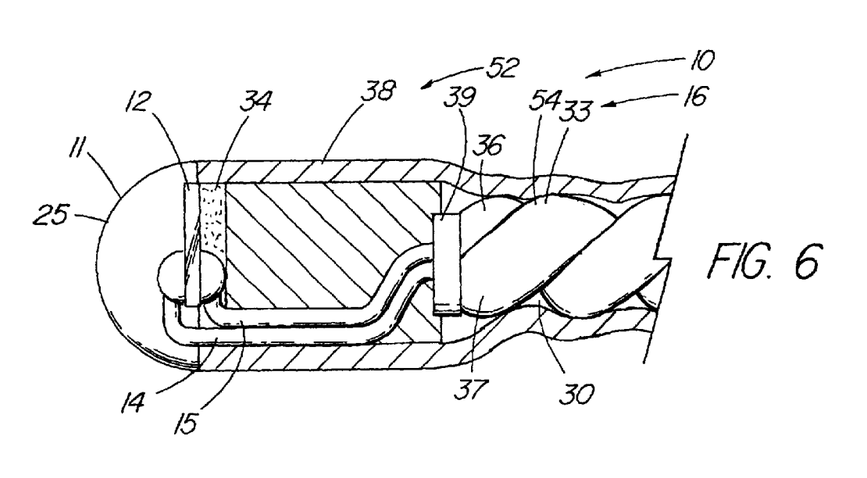
FIG. 6 depicts a partially sectioned side view of an embodiment wherein the malleable portion comprises a portion of the conductor means.

FIGS. 5–6 depict embodiments in which the shapeable portions are created by a means other than a hollow metal cannula. In FIG. 5, a solid core member 33, made of a malleable, shapeable material such as annealed stainless steel, comprises the shapeable portion 16 of the probe. Rather than placing the conductor means 13 through the shapeable portion 16, the wires 14, 15 comprising the conductor means 13 are placed on the outside of the core member 33, e.g., wrapped helically as in the illustrative example, and protected by the outer sheath 17, which comprises a flexible outer sleeve or jacket 38, which may include coating (e.g, dip coat) of a standard medical grade polymer, such as urethane, silicone, or PTFE. This outer sleeve 38 can, in turn, be surface treated to make it more lubricious by one of a variety of well known means, or it can be bonded to an agent for increasing lubricity or which serves another clinical purpose, such as a medicament of some type. The diameter of the core member 33 required to achieve a shapeable portion that is sufficiently, but not overly malleable, depends on the type of metal used, the degree of annealing, and the thickness and type of the outer layer used. The outer sleeve 38 (and hence, the outer sheath 17) can be eliminated if another means of securing and protecting the wires 14, 15 is used such as bonding the wires directly to the core member 33 with an adhesive. Additionally, one or more grooves (not shown) can be formed in the outer surface of the core member 33 to receive and protect the fragile wires 14, 15 as they extend thereal­ong.

In a related embodiment, the core member 33 can com­prises a plurality of elements that are intertwined to form the shapeable portion 16. Such an intertwined member 54 is shown in FIG. 6 which differs from previous embodiments in that the shapeable portion 16 also serves as a portion of the conductor means 13, thereby eliminating the need for a separate element to fulfill this function. In the illustrative embodiment, the the first and second wires 14, 15 include larger diameter, shapeable first and second wires 36, 37 that are coupled to the smaller distal portion of the first and second wires 14, 15 and form the intertwined member 54 comprising the shapeable portion 16 of the probe 10. Each pair of different sized wires are joined with a connector means 39 such as a wire crimp, solder joint, or other well known connector. The first and second shapeable wires 36, 37 of the intertwined member 54 contain external insulation, typically a polymer such as PTFE, or are insulated in some other manner such as by a plastic spacer material. In the illustrative embodiment, an optional outer sleeve 38 (outer sheath 17), such as polymer tubing, can provide additional support and protection to the wires and connections. In a related embodiment, but unillustrated embodiment, the same small wires 14, 15 (e.g, 36 AWG) that comprise the con­ductor means 13 and that attach directly to the ultrasonic transducer, can be combined with an intertwined bundle of similar small wires to form the intertwined member 54, the other wires serving only as individual components of the core members 33 rather than being part of the conductor means 13. As long as the conductor wires 14, 15, are insulated, the other wires of the intertwined member 54 do not have to be electrically insulated from one another. Although as with other embodiments, there are several variables involved in constructing a desirable probe, it is important to note that one skilled in the art could easily determine the gauge, type, and number of wires necessary to achieve the proper malleability characteristics without undue experimentation being required.

Figure 7:
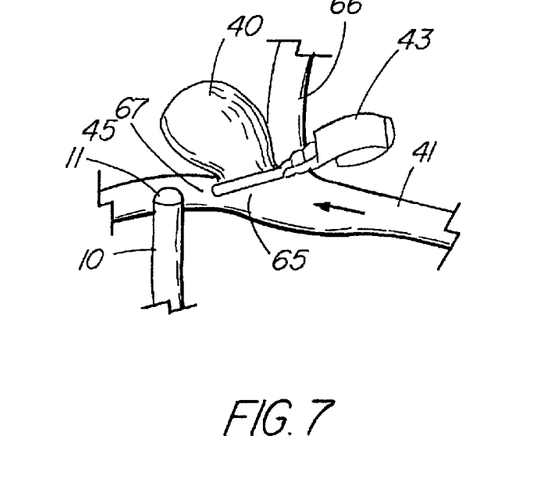
FIGS. 7 depicts the present invention being used to detect blood flow in a cerebral vessel.

FIG. 7 depicts the probe 10 of the present invention being used on a cerebral artery 41 within the brain in conjunction with a procedure to apply an aneurysm clip 43 to isolate an aneurysm 40 from the parent vessel 65. In the illustrative example, the clip 43 has been applied to the parent vessel 65 of the aneurysm 40; however, a portion of the parent vessel 65 has been clipped as well, causing a partial or full occlusion 67 of the vessel. By placing the probe 10 at a reading site 45 downstream of the clip 43, the clinician can determine that blood has been compromised and the clip 43 can be reapplied. Reference measurements before and after clipping can help the clinician determine whether indeed, the clip has been incorrectly applied. In the illustrative clinical situation, another site that may be important to read would be a point along the adjacent branch vessel 66 to ensure that the clip 43 did not inadvertently occlude that vessel. In embodiments designed to work with the COOK® Vascular Blood Flow Monitor, or a similar type of unit, the operator listens for an audible signal of noise, indicating that the Doppler signals detect movement, and thus, blood flow within the underlying vessel. If the audible signals are comparable to the pre-clip level, it confirms that the vessel continues to have normal patent flow.

Figure 8:
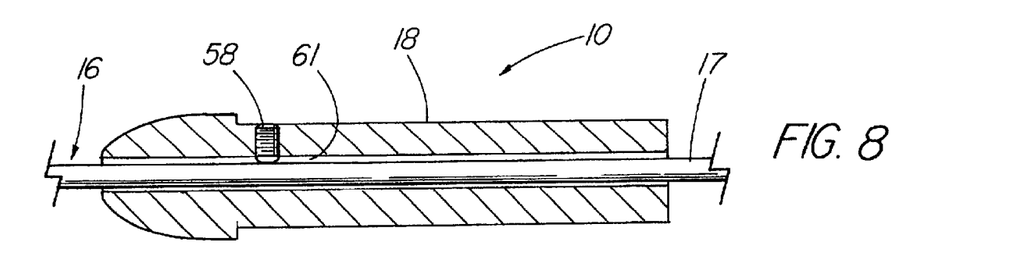
FIG. 8 depicts a partially sectioned view of an adjustable handle embodiment of the present invention.

FIG. 8 depicts an embodiment of the present invention wherein the handle portion 18 can be positioned along the malleable sheath 17, thereby adjusting the length of the shapable portion 16 to conform to differing anatomical sites or to suit the preferences of the physician. In the illustrative embodiment, a tightening mechanism 58, such as the illus­trative set screw, is used to secure the handle 18 to the malleable sheath 17; however, a collet, or some other well know mechanism for allowing the handle to engage with the sheath 17 may be substituted. In addition, the malleable sheath 17 may include structure, such as indentations, teeth or other projections, etc., that could engage with cooperating structure located within the internal passageway 61 of the handle to assist in securing the handle 18.

Figure 9:
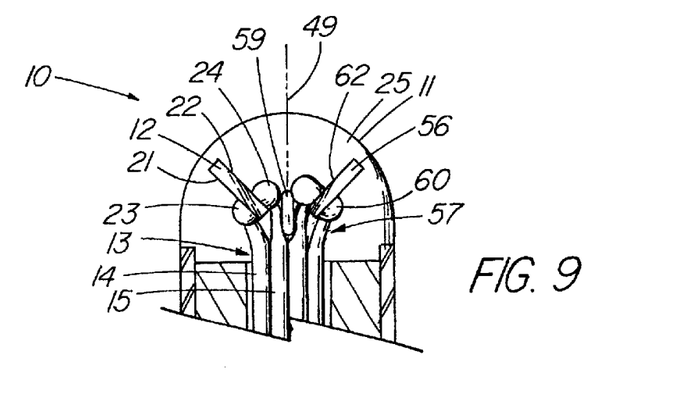
FIG. 9 depicts a partially sectioned side view of an embodiment of the present invention that includes two ultrasonic transducer crystals.

The embodiments of FIGS. 1–6 depict an embodiment of the present invention in which there is a single ultrasonic transducer 12 located within the transducer head 11 to detect and confirm the presence of flow within a vessel. It is well known in the art that using two ultrasonic transducers allows the probe to measure the actual rate of flow within a vessel if connected to an external flowmeter unit designed to generate and process the dual signals to provide the quan­titative measurement. FIG. 9 depicts a transducer head 11 of the present invention comprising a first ultrasonic transducer 12 oriented approximately 45° with respect to the longitu­dinal axis 49 of the probe 10 and a second ultrasonic transducer 56, also oriented approximately 45° with respect to the longitudinal axis 49 and oriented approximately 90° with respect to the first ultrasonic transducer. This orienta­tion permits the signal from the second operative face 22 of the first ultrasonic transducer 12 and that from the first operative face 62 of the second ultrasonic transducer 56 to simultaneously enter the vessel for a real-time reading of actual blood flow. An example of an intraoperative surgical flowmeter capable of measuring true volume flow would be the Transonic Flow-QC Surgical Flowmeter (Transonic Sys­tems Incorporated, Ithaca, N.Y.). The first ultrasonic trans­ducer 12 includes first and second solder joints 23, 24 with respective wires 15, 16 extending therefrom, while the second ultrasonic transducer 56 comprises a similar con­figuration that includes the solder joint 60 and second conductor 57 extending therefrom. In the illustrative example, an insulator 59 is positioned between the respec­tive solder joints 22, 24 and 60.

While discussion has focused on use of the present Doppler probe to maneuver within the tight confines of the brain to confirm cerebral vessel blood flow, the invention has may potential clinical uses in monitoring blood flow within selected vessels or other bodily fluid conduits within the body of a patient, especially when access to these sites is difficult and requires tight angles of approach. For example, other possible clinical uses of this invention could include arterial flow monitoring in coronary arterial bypass graft procedures (CABG). Another possible use would be in an endarterectomy procedure to monitor carotid arterial flow. In such an instance, it might prove useful to leave the distal portion of the device partially implanted within the patient for a short duration, much like an intravascular needle is done. Additional embodiments might be utilized with different Doppler signal generators and processors capable of more sophisticated monitoring such as actual quantification of flow, thus possibly requiring appropriate modifications of the probe that would still fall within the spirit of this invention and the scope of the claims.

Any other undisclosed or incidental details of the construction or composition of the various elements of the disclosed embodiments of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure.

What is claimed is:

1. A medical probe for detecting flow of blood within a vessel of a patient during a medical procedure, the probe having a distal end and comprising:
    a transducer head that includes an ultrasonic transducer adjacent the distal end of the probe, the ultrasonic transducer adapted for generating signals in response to blood flow within vessel;
    an electrical conductor having a first end and a second end, the first end being operatively connected to the ultrasonic transducer and the second end being connectable to a unit for processing flow-responsive signals;
    a handle portion; and
    a shapeable portion extending proximally from adjacent the distal end of said probe, said transducer head and said shapeable portion and said transducer head being substantially isodiametric, said shapeable portion being a plastically deformable cannula.

2. The medical probe of claim 1, wherein the shapeable portion comprises a metal cannula.

3. The medical probe of claim 2, wherein the metal cannula comprises annealed stainless steel.

4. The medical probe of claim 1, wherein the transducer head is moveable relative to the distal end of the shapeable portion.

5. The medical probe of claim 4, wherein the transducer head is adapted to at least partially reside within the shapeable portion and is at least partially extendable from the distal end thereof.

6. The medical probe of claim 6, wherein the transducer head includes an encasing material surrounding the ultrasonic transducer.

7. The medical probe of claim 6, wherein the encasing material includes an epoxy material.

8. The medical probe of claim 1 further including a longitudinal axis, wherein the ultrasonic transducer includes a first operative surface, the first operative surface of the ultrasonic transducer being oriented approximately perpendicular with respect to the longitudinal axis of the medical probe.

9. The medical probe of claim 1 further including a longitudinal axis, wherein the ultrasonic transducer includes a first operative surface, the first operative surface of the ultrasonic transducer being oriented approximately parallel with respect to the longitudinal axis of the medical probe.

10. The medical probe of claim 1, wherein the electrical conductor comprises a first and a second wire attached to the ultrasonic transducer.

11. The medical probe of claim 10, wherein the first and second wires include shapeable wire.

12. The medical probe of claim 1, wherein the shapeable portion comprises a malleable core wire, wherein the electrical conductor is located thereabout.

13. The medical probe of claim 12, wherein the electrical conductor comprises a first and a second wire helical wrapped about the malleable core wire, the medical probe further including an outer sheath disposed over the shapeable portion.

14. The medical probe of claim 1, wherein the transducer head includes a plurality of ultrasonic transducers.

15. The medical probe of claim 14 comprising a first and a second ultrasonic transducer oriented approximately 90° with respect to one another.

16. The medical probe of claim 15 further including a longitudinal axis, wherein the first and second ultrasonic transducers are oriented approximately 45° with respect to the longitudinal axis.

17. The medical probe of claim 1, wherein said shapeable portion comprises an annealed, malleable metal.

18. The medical probe of claim 1, wherein said shapeable portion extends proximally from adjacent the distal end of said probe to said handle portion.

19. A medical probe for detecting flow of blood within a bodily passage, the probe comprising:
    a transducer head that includes an ultrasonic transducer having a first operative surface;
    an electrical conductor comprising two wires, each wire having a first end and a second end, the first ends being operatively connected to the ultrasonic transducer, and the second ends being connectable to an external source unit adapted to generate and process Doppler signals in response to blood flow within the bodily passage;
    a handle portion;
    an outer sheath connected to the handle portion and at least partially housing the electrical conductor, the distal portion of the outer sheath, which extends distally from the handle portion, at least partially comprising a shapeable portion having a distal end, the shapeable portion being capable of retaining a formed shape as the probe is manipulated within the bodily passage; the transducer head being affixed about the distal end of the shapeable portion, said handle portion slidable relative to the shapeable portion such that the length of the shapeable portion can be adjusted by an operator of the medical probe.

20. The medical probe of claim 19, wherein the shapeable portion includes a length of annealed stainless steel tubing.

21. The medical probe of claim 19, wherein the ultrasonic transducer further includes a second operative surface.

22. The medical probe of claim 19 wherein the handle portion includes a tightening mechanism to secure the handle to the outer sheath.

23. The medical probe of claim 19, wherein said outer sheath of formed of a malleable material.

24. The medical probe of claim 19, wherein said outer sheath comprises an annealed metal cannula.

25. A medical probe for detecting flow of fluid within a bodily passage, the probe having a longitudinal axis and comprising:
    a transducer head that includes at least one ultrasonic transducer having a first operative surface that is perpendicular to the longitudinal axis of the probe, the transducer head including an epoxy encasing material therearound;
    an electrical conductor, comprising two wires, each having a first end and a second end, the first ends being soldered to the ultrasonic transducer, and the second ends being connectable to an external source unit adapted to generate and process Doppler signals;

a handle portion;

an outer sheath comprising an annealed metal cannula that is connected to the handle portion that at least partially houses the electrical conductor, wherein that portion of the outer sheath that extends distally from the handle portion comprises a shapeable portion, the shapeable portion having a distal end, the transducer head being affixed about the distal end of the shapeable portion; and wherein the handle portion is slidable relative to the shapeable portion, such that the length of the shapeable portion can be adjusted by an operator of the medical probe.

26. A method for detecting the flow of blood within a vessel of a patient during a medical procedure, comprising:

providing a medical probe having a proximal end and a distal end, the medical probe comprising a transducer head that includes an ultrasonic transducer adjacent the distal end of the medical probe, and further comprising a shapeable portion that extends proximally from adjacent the distal end, the shapeable portion and transducer head being substantially isodiametric, and being sized and dimensioned for introduction into the natural spaces of the brain, the shapeable portion being plastically deformable into a desired contour by an operator prior to the medical procedure;

deforming the shapeable portion of said medical probe to conform to an anatomical site;

introducing the deformed medical probe into the anatomical site;

directing ultrasonic energy from said transducer to said vessel for generating signals responsive to blood flow within said vessel; and receiving and processing said signals to detect blood flow within said vessel.

27. The method of claim 26, wherein said anatomical site comprises the natural spaces within the brain, and said medical probe is sized and dimensioned for introduction into said natural spaces.

28. The method of claim 27, wherein the medical probe further comprises an electrical conductor having a first end and a second end, the first end being operatively connected to the ultrasonic transducer and the second end being connectable to a unit for receiving and processing said signals.

29. The method of claim 26, wherein the transducer head includes an encasing material.

30. The method of claim 29, wherein the encasing material comprises an epoxy material.

31. The medical probe of claim 26, wherein the shapeable portion comprises a metal cannula.

32. The medical probe of claim 26, wherein the transducer head is moveable relative to the distal end of the shapeable portion.

33. A medical probe for detecting flow of blood within a bodily passage, the probe having a distal end and comprising:

a transducer head that includes an ultrasonic transducer adjacent the distal end of the probe, the ultrasonic transducer adapted for generating signals in response to blood flow within said bodily passage, the transducer head including an encasing material surrounding the ultrasonic transducer;

an electrical conductor having a first end and a second end, the first end being operatively connected to the ultrasonic transducer, and the second end being connectable to a unit for processing flow-responsive signals;

a handle portion; and a shapeable portion extending distally from said handle portion said shapeable portion and said transducer head being sized to provide a substantially smooth diametric transition therebetween, said shapeable portion being a plastically deformable cannula.

34. The medical probe of claim 33, wherein the shapeable portion comprises a metal cannula.

35. The medical probe of claim 33, wherein the transducer head is moveable relative to the distal end of the shapeable portion.

36. The medical probe of claim 35, wherein the transducer head is adapted to at least partially reside within the shapeable portion and is at least partially extendable from the distal end thereof.

37. The medical probe of claim 33, wherein the encasing material comprises an epoxy material.

38. The medical probe of claim 33, further including a longitudinal axis, wherein the ultrasonic transducer includes a first operative surface, the first operative surface of the ultrasonic transducer being oriented approximately perpendicular with respect to the longitudinal axis of the medical probe.

39. The medical probe of claim 33, further including a longitudinal axis, wherein the ultrasonic transducer includes a first operative surface, the first operative surface of the ultrasonic transducer being oriented approximately parallel with respect to the longitudinal axis of the medical probe.

40. The medical probe of claim 33, wherein the electrical conductor comprises a first and second wire attaced to the ultrasonic transducer.

41. The medical probe of claim 40, wherein the first and second wires include shapeable wire.

42. The medical probe of claim 33, wherein the shapeable portion comprises a malleable core wire, wherein the electricla conductor is located thereabout.

43. The medical probe of claim 42, wherein the electrical conductor comprises a first and second wire helical wrapped about the malleable core wire, the medical probe further including an outer sheath disposed over the shapeable portion.

44. The medical probe of claim 33, wherein the transducer head includes a plurality of ultrasonic transducers.

45. The medical probe of claim 44, comprising a first and a second ultrasonic transducer oriented approximately 90° C. with respect to one another, 46. The medical probe of claim 45, further including a longitudinal axis, wherein the first and second ultrasonic transducers are oriented approximately 45° C. with respect to the longitudinal axis.

* * * * *

UNITED STATES PATENT AND TRADEMARK OFFICE
CERTIFICATE OF CORRECTION

PATENT NO.        : 6,974,416 B2
APPLICATION NO.   : 09/925693
DATED             : December 13, 2005
INVENTOR(S)       : Booker et al.

It is certified that error appears in the above-identified patent and that said Letters Patent is hereby corrected as shown below:

<u>Title Page,</u>
Before line 1, under "U.S. PATENT DOCUMENTS", insert the following:

| | | |
|---|---|---|
| --4,142,412 | 03/1979 | McLeod et al. |
| 4,771,788 | 09/1988 | Millar |
| 4,887,606 | 12/1989 | Yock et al. |
| 4,920,967 | 05/1990 | Cottonaro et al. |
| 4,945,896 | 08/1990 | Gade |
| 5,038,789 | 08/1991 | Frazin |
| 5,058,595 | 10/1991 | Kern |
| 5,119,821 | 06/1992 | Tuchler |
| 5,144,955 | 09/1992 | O'Hara |
| 5,220,924 | 06/1993 | Frazin |
| 5,360,406 | 11/1994 | Boykin et al. |
| 5,431,628 | 07/1995 | Millar |
| 5,433,205 | 07/1995 | Visveshwara |
| 5,464,016 | 11/1995 | Nicholas et al. |
| 5,588,436 | 12/1996 | Narayanan et al. |
| 5,654,539 | 08/1997 | Borgos at al. |
| 5,680,865 | 10/1997 | Tanaka |
| 5,865,828 | 02/1999 | Jeng |
| 6,093,150 | 07/2000 | Drost et al. -- |

Delete reference
"6,216,233 B1  4/2001        Baweja"
Replace it with
-- 6,261,233    07/2001      Kantorovich --

<u>Column 9,</u>
Line33, in Claim 1 delete "and said transducer head"
Line 34, in Claim 1 after "shapeable portion" add -- and said transducer head --
Line 34, in Claim 1 after "being" add -- sized and dimensioned for introduction into natural spaces within the brain to monitor flow through a vessel located therein, the shapeable portion being --
Line 35, in Claim 1 delete "a"
Line 35, in Claim 1 after "deformable" delete "cannula" and add -- into a desired contour by an operator prior to the medical procedure, and capable of resisting substantial further deformation by contact with brain tissue as the probe is navigated therethrough. --
Line 47, in Claim 6 after "probe of claim" change "6" to -- 1 --

UNITED STATES PATENT AND TRADEMARK OFFICE
CERTIFICATE OF CORRECTION

| | | |
|---|---|---|
| PATENT NO. | : 6,974,416 B2 | Page 2 of 2 |
| APPLICATION NO. | : 09/925693 | |
| DATED | : December 13, 2005 | |
| INVENTOR(S) | : Booker et al. | |

It is certified that error appears in the above-identified patent and that said Letters Patent is hereby corrected as shown below:

Column 12,
Line 41, in Claim 40 change "attaced" to -- attached --
Line 58, in Claim 45 remove "C."
Line 61, in Claim 46 remove "C."

Signed and Sealed this

Fourth Day of September, 2007

JON W. DUDAS
*Director of the United States Patent and Trademark Office*